United States Patent
Mercado

(10) Patent No.: US 9,261,354 B1
(45) Date of Patent: Feb. 16, 2016

(54) SYSTEM AND PROCESS FOR MEASURING DEFLECTION

(71) Applicant: Edward J. Mercado, Seabrook, TX (US)

(72) Inventor: Edward J. Mercado, Seabrook, TX (US)

(*) Notice: Subject to any disclaimer, the term of this patent is extended or adjusted under 35 U.S.C. 154(b) by 0 days.

(21) Appl. No.: 14/523,279

(22) Filed: Oct. 24, 2014

(51) Int. Cl.
| | |
|---|---|
| *G01B 11/14* | (2006.01) |
| *G01B 11/16* | (2006.01) |
| *G01N 3/00* | (2006.01) |
| G01B 11/24 | (2006.01) |
| G01B 11/03 | (2006.01) |

(52) U.S. Cl.
CPC ...... *G01B 11/16* (2013.01); *G01N 3/00* (2013.01); *G01B 11/03* (2013.01); *G01B 11/167* (2013.01); *G01B 11/24* (2013.01)

(58) Field of Classification Search
CPC ...... G01B 11/16; G01B 11/167; G01B 11/24; G01B 11/30; G01N 3/00
USPC ............................................. 356/614, 615
See application file for complete search history.

(56) References Cited

U.S. PATENT DOCUMENTS

| | | | |
|---|---|---|---|
| 3,383,913 | A | 5/1968 | Swift |
| 3,427,877 | A | 2/1969 | Swift et al. |
| 4,571,695 | A | 2/1986 | Elton et al. |
| 4,788,859 | A | 12/1988 | Khattak |
| 5,046,366 | A | 9/1991 | Basson et al. |
| 5,753,808 | A | 5/1998 | Johnson |
| 6,119,353 | A | 9/2000 | Gronkov |
| 8,596,116 | B2 | 12/2013 | Ullidtz |
| 2002/0093664 | A1* | 7/2002 | Max ............... G01B 11/2504 356/601 |
| 2012/0010828 | A1 | 1/2012 | Ullidtz |

* cited by examiner

*Primary Examiner* — Kara E Geisel
*Assistant Examiner* — Hina F Ayub
(74) *Attorney, Agent, or Firm* — Egbert Law Offices, PLLC

(57) ABSTRACT

A system for measuring a deflection has a base, a first laser directed downwardly toward an underlying surface at an acute angle, a second laser in spaced relation to the first laser and directed downwardly toward the underlying surface at an approximately vertical angle, a third laser affixed to the base in spaced relation to the second laser and directed downwardly toward the underlying surface at an acute angle in a direction toward the second laser, a camera directed toward the points of reflectance of the lasers with the underlying surface, and a processor cooperative with the camera so as to measure a distance between the points of reflectance of the first and second lasers and measuring the distance between the points of reflectance of the second and third lasers. The processor compares the measured distances so as to produce an angle of deflection of the underlying surface.

20 Claims, 3 Drawing Sheets

SYSTEM AND PROCESS FOR MEASURING DEFLECTION

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to the measurement of the deflection of underlying surfaces. More particularly, the present invention relates to systems and processes for measuring the angle of deflection of the rail or pavement when subjected to the load of a wheel. Additionally, the present invention relates to laser-based systems for measuring such deflections.

2. Description of Related Art Including Information Disclosed Under 37 CFR 1.97 and 37 CFR 1.98.

The loadbearing capability for pavements and rails may deteriorate, over time, due to a number of factors, including changes in the elastic moduli of subpavement layers of earth. In order to determine pavement conditions for highways, the loadbearing capability of the pavement can be periodically tested. In order to measure the loadbearing capability of the pavement, it is desirable to utilize technologies that are non-destructive so that the integrity of the pavement layers is maintained. Further, it is important that the measurement should be made rapidly, through an automated system, so as to minimize time and reduce costs.

Different methods have been developed for the non-destructive testing of pavements, with one utilizing a falling weight dropped on the pavement from a stationary platform. Sensors than measure the deflection of the pavement at intervals out from the falling weight. Systems utilizing this method of time commonly referred to as falling weight deflectometers.

Other systems utilize a fast-moving, heavy wheel load that rolls along the pavement, with sensors being arranged at intervals out from the wheel to measure deflections. Systems utilizing this approach are commonly referred to as rolling wheel deflectometers. In essence, a load is placed on a wheel that rolls across the pavement and the depth of a deflection basin created by the loaded wheel is measured using precision laser sensors mounted on a horizontal member that tracks with the wheel. Such deflection measurements provide insight into the loadbearing capability of the pavement.

The current technology is very limited in the measurement of pavement deflections. Measurements of deflection can vary between 20 and 50% between falling weight deflectometers, and rolling wheel deflectometers depending on pavement temperature, texture, stiffness, composition, and deflection magnitude. Rolling wheel deflectcometers provide measurements that are combination of deflection, load and texture. The measured deflection is the sum of the actual pavement deflection and the vertical vibration of the layers mounted onto the vehicle.

An area of concern with rolling wheel deflectometers is the compromise between precision and the loss of details associated with spatial averaging. This is of particular concern with measurements that are being taken at high speeds. In general, an averaging of approximately ten meters or more is required in order to reduce the large random errors in the individual measurements caused by bouncing, texture and vibrations of the vehicle.

In addition to the major detrimental effects of vibration and texture, two additional forces require evaluation as the velocity of data acquisition increases. In particular, there can be sideways sway or "rock 'n roll" as the vehicle travels. This lateral shifting exerts a time-varying load on the wheels from side-to-side. If this vehicle is also measuring deflection, either on rails or pavement, then the measured deflection needs to be corrected for the time-varying load. Current practice ignores this effect and assumes the load is constant.

Additionally, at current load data acquisition speeds, the deflection basin is assumed to be symmetrical about the load wheel and back calculations are used to obtain pavement (or railbed) parameters based on a "static load" model. As data acquisition speeds increase, the static model becomes less viable and the deflection basin formed by the moving load will not be symmetrical.

The texture problem fundamentally exists because the diameter of the laser beams is small compared to the irregularities in the pavement surface. This problem is exacerbated by the deliberate efforts to roughen the pavement surface in order to increase water drainage and traction between tires and pavement surface. Further exacerbation is caused by deterioration of the pavement through patching and cracking.

The effective vertical vibration on the total deflection measurement is more difficult to isolate and evaluate. The railroad industry has an analogous problem to the pavement management fraternity where track modulus is analogous to pavement deflection. Rail and pavement deflection measures the competence of the structure supporting the rolling loads, either trains or vehicles. The major difference in noise problems (i.e. vertical vibration and texture) based by rail and pavement engineers is that the smooth rail track surface does not have the texture problem built into pavement surfaces.

As the pavement surface quality deteriorates, deflection measurement quality also deteriorates from a combination of surface reflectance quality, increased roughness and increased vertical vibration. One rolling wheel deflectometer problem is the vertical vibration of the railcar or trailer holding the lasers. Rough pavement primarily affects the pavement deflectometer. Hence, the noise level measured by the railcar deflectometer is a good measure of the vertical vibration component in the rolling wheel deflectometer measurements. An additional problem is the combination of deflection and surface texture. As pavement ages and the surface deteriorates, laser reflectivity rapidly degrades, making accurate measurements problematic. The vertical vibration component of the measurement noise also increases rapidly with deteriorating pavement surface quality.

In the past, various patents have issued with respect to the measurement of pavement deflection.

For example, U.S. Pat. No. 3,383,913, issued a May 21, 1968 to G. Swift, is an early patent disclosing measurement of pavement deflection. In this patent, a moving vehicle applies a load to the underlying surface. A first carriage is moved by the vehicle having a structural displacement sensing device mounted thereon which is adapted to sense structure displacement near the point of application of the load. A second carriage is moved by the vehicle simultaneously with the first carriage. The second carriage also has a displacement sensing device adapted to sense structural displacement sufficiently removed from the point of application of the load to the structure so as to be unaffected by the load. Suitable electrical signals are transmitted so as to be indicative of the deflection.

U.S. Pat. No. 3,427,877, issued on Feb. 18, 1969 to Swift et al., discloses a dynamic deflection determination device. This device includes a two-wheeled trailer and a force applying assembly mounted to the trailer. A motion sensing device detects deflections of the structure resulting from the application of a cyclic force. The motion sensing device is mechanically coupled to the structure. Electrical signals are transmitted indicative of the movement detected by the motion sensing device.

U.S. Pat. No. 4,571,695, issued on Feb. 18, 1986 to Elton et al., discloses a non-contact road profilometer and deflection meter. This apparatus includes a rigid frame attached to a vehicle, first, second and third profile detecting means, and a controller for simultaneously instructing the profile detecting means to activate to cause the distance to be simultaneously measured between the frame and the underlying road surface at three laterally spaced-apart locations. This provides a set of distance data.

U.S. Pat. No. 4,788,859, issued on Dec. 6, 1988 to A. S. Khattak, shows a method for direct measurement of the vertical displacement of a point on a surface of the pavement upon application of a load thereto. The method measures the vertical displacement through the use of optical equipment. The displacement is equivalent to the vertical movement of an optical focusing element between the position of the element when a point on the surface of the pavement is in focus with and without the application of the load. The point linear displacement measurement can be applied to the calculation of a volumetric displacement.

U.S. Pat. No. 5,046,366, issued on Sep. 10, 1991 to Basson et al., shows a method for measuring deflection or deformation in pavement structures. The system includes at least one apparatus including an electric coils sensitive to relative movement between them at a relatively anchored body of ferromagnetic material. A pair of longitudinally-spaced relatively movable discs and a body of resilient transversely extendable material is positioned between the discs. A nut serves to urge the discs toward one another so as to cause the body transversely to expand to secure the apparatus at a predetermined depth against a wall in a test hole.

U.S. Pat. No. 6,119,353, issued on Sep. 19, 2000 to L. Gronkov, discloses a method and apparatus for non-contact measuring of the deflection of roads or rails. This equipment includes a self-propelled vehicle with a load which influences at least one wheel. The speed of the wheel is measured in the direction of travel. A laser device includes at least one electromagnetic beam directed toward the roadway in the vicinity of the vehicle. A Doppler frequency change in the reflection is detected. An electronic circuit continuously registers the results of the measurements and, as such, the deflection at a normal traveling speed.

U.S. Pat. No. 5,753,808, issued on May 19, 1998 R. F. Johnson, teaches a self-compensating rolling weight deflectometer for the measurement of a pavement under load. The deflectometer incorporates an alignment laser beam emitter that measures vertical displacement of each of the plurality of distance sensors is mounted on a horizontal sensor bearer member that bends or vibrates as it is transported over a pavement for deflection measurement. The measured vertical displacements, due to member bending, allows the deflectometer to compensate for errors introduced by member bending and thereby provide a more accurate measurement of pavement deflection.

U.S. Pat. No. 8,596,113, issued on Dec. 3, 2013 P. Ullidtz, provides an improved non-destructive testing of pavements using rolling wheel deflectometers having more than four sensors. The additional sensors accurately detect pavement deflections under load by compensating for the influence of the load deflection basin. The sensors are positioned beyond the wheel load. The sensors are spaced with equal distances from the rolling weight and can have a distance between adjacent sensors that is greater than the equivalent thickness of the pavement being measured.

U.S. Patent Publication No. 2012/0010828, published on Jan. 12, 2012 P. Ullidtz, describes a rolling weight deflectometer having sensors to measure pavement deflection. The sensors provide test data to determine the subgrade modulus and equivalent thickness of the pavements. This information is then utilized to determine more than deflection and is utilized to determine critical strain parameters so as to predict bearing capacity, rutting and roughness characteristics of pavements.

It is an object of the present invention to provide a system and process for measuring deflection which avoids the problems associated with vertical vibration of the sensors.

It is another object of the present invention to provide a system and process for measuring deflection that overcomes the effect of texture and reflectance quality on laser spot reflectivity.

It is another object of the present invention to provide a system and process for measuring deflection which avoids corruption of pavement deflection measurement.

It is another object of the present invention to provide a system and process for measuring deflection which dynamically measures load.

It is another object of the present invention to provide a system and process for measuring deflection that eliminates vertical vibration noise components.

It is still a further object of the present invention to provide a system and process for the measuring of deflection which measures the angle of deflection in order to calculate the amount of deflection.

These and other objects and advantages of the present invention will become apparent from a reading of the attached specification and appended claims.

BRIEF SUMMARY OF THE INVENTION

The present invention is a system for measuring a deflection of an underlying surface. The system comprises a base, a first laser affixed to the base, a second laser affixed to the base, a third laser affixed to the base, a camera, and a processor cooperative with the camera so as to measure distances between the point of reflectance of the lasers. In particular, the first laser is directed downwardly toward the underlying surface at an acute angle relative to the base. The second laser is positioned in spaced relationship to the first laser on one side of the first laser. The second laser is directed vertically downwardly toward the underlying surface in an arrangement approximately transverse to the base. The third laser is positioned in spaced relationship to the second laser on the side of the second laser opposite the first laser. The third laser is directed downwardly toward the underlying surface at an acute angle relative to the base in a direction toward the second laser. The camera is directed downwardly toward the points of reflectance of the first, second and third lasers with the underlying surface. The processor is cooperative at the camera so as to measure a distance between the point of reflectance of the first laser with the underlying surface and the point of reflectance of the second laser with the underlying surface and also to measure a distance between the point of reflectance of the second laser with the underlying surface in the point of reflectance of the third laser with the underlying surface. The processor compares the measured distances so as to produce an angle of deflection of the underlying surface.

In the present invention, a vehicle is employed that has at least one wheel. The vehicle has a frame. The base is affixed to the frame such that the first, second and third lasers are directed toward the underlying surface adjacent to the wheel. The vehicle can be a truck and the underlying surface is a pavement. In another embodiment, the vehicle can be a train and the underlying surface can be a rail.

The acute angle of the first laser is approximately identical to the acute angle of the third laser. In particular, the acute angle of the first laser is approximately 45° and the acute angle of the third lasers is also approximately 45°.

The camera obtains a plurality of images of the points of reflectance of the first, second and third lasers as the vehicle moves along the underlying surface. The processor compares the measured distances of the first image to the second image and the distance from the second image to the third image so as to produce the angle of deflection. In particular, the processor determines the angle of deflection in accordance with a formula:

$$\text{Tan}(\beta) = -\text{Tan}(\alpha) \times (c-d)/(c+d)$$

where β as the angle of deflection, α is the acute angle of the first and third lasers, c is the distance between the points of reflectance of the first and second lasers, and d is the distance between the points of reflectance of the second and third lasers.

In another embodiment of the present invention, a crossmember extends in transverse relationship to the base. A fourth laser is affixed to the crossmember and directed downwardly toward the underlying surface in a direction toward the second laser. The fourth laser is in spaced relationship to the second laser. A fifth laser is affixed to the crossmember and directed downwardly toward underlying surface in a direction toward the second laser. The fifth laser is positioned in spaced relationship to the second laser on a side of the second laser opposite the fourth laser. The camera is directed downwardly so as to capture the points of reflectance of the fourth and fifth lasers with the underlying surface.

In the present invention, the vehicle has an upper frame in a lower frame with one or more springs resiliently mounted therebetween. A sensor is cooperative with the upper frame and the lower frame so as to measure a displacement between the upper frame and the lower frame. The processor is cooperative with the sensor so as to measure a load of the wheel upon the underlying surface. In particular, the processor measures the load of the wheel in accordance with:

$$F = kX$$

in which F is the force on the wheel, k is a spring constant of the spring, and X is the measured displacement between the upper frame and the lower frame.

The present invention is also a process for measuring a deflection of an underlying surface under a load. This process includes the steps of: (1) directing a first laser toward the underlying surface at an acute angle so as to produce a point of reflectance of the first laser on the underlying surface; (2) directing a second laser vertically downwardly toward the underlying surface so as to produce a point of reflectance of the second laser on the underlying surface; (3) directing a third laser toward the underlying surface at an acute angle toward the second laser so as to produce a point of reflectance of the third laser on the underlying surface; (4) measuring a distance between the point of reflectance of said first laser and the point of reflectance of said second laser; (5) measuring a distance between the point of reflectance of said third laser and the point of reflectance of said second laser; and (6) comparing the distances so as to produce a distance from the lasers to the underlying surface by triangulation.

The process of the present invention further includes moving a vehicle along the underlying surface such that the vehicle has a wheel deflecting the underlying surface. The first, second and third lasers are connected to the vehicle. The first, second and third lasers are directed toward the underlying surface in an area adjacent to the wheel. The acute angles of the first and third lasers are approximately equal.

The method of the present invention further includes measuring a load of the wheel upon the underlying surface. In particular, the vehicle has an upper frame and a lower frame with one or more springs resiliently mounted therebetween. The step of measuring includes measuring the displacement of the upper frame with respect to the lower frame and comparing the measured distance with a spring constant of the spring so as to determine the load of the wheel on the underlying surface.

This foregoing Section is intended to describe, with particularity, the preferred embodiments of the present invention. It is understood that modifications to these preferred embodiment can be made within the scope of the present invention. As such, this Section should not be construed, in any way, as limiting of the broad scope of the present invention. The present invention should only be limited by the following claims and their legal equivalents.

DETAILED DESCRIPTION OF THE INVENTION

Figure 1:
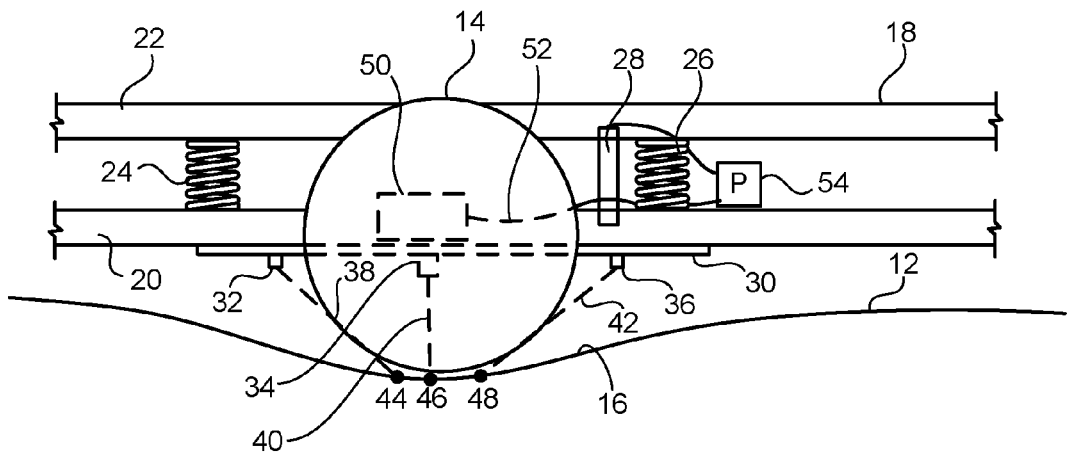
FIG. 1 is a side elevational view showing the application of the system of the present invention upon a vehicle.

Referring to FIG. 1, there is shown the system 10 for the measurement of the deflections of an underlying surface. In particular, the underlying surface 12 is illustrated as a section of pavement. However, within the concept of the present invention, the underlying surface 12 can also be a rail. A wheel 14 under a load is illustrated as rolling along the underlying surface 12. In particular, the wheel 14 can be part of a truck or a rail car. Typically, for the measurement of pavement, the wheel 14 should support between 20,000 and 40,000 pounds of weight. As such, this substantial amount of weight can create a deflection 16 in the underlying surface 12.

The wheel 14 is supported by a vehicle 18. The vehicle 18 includes a lower frame 20 and an upper frame 22. A first spring 24 is positioned between the lower frame 20 and the upper frame 22. Another spring 26 extends between the lower frame 20 and the upper frame 22. Springs 24 and 26 will have a known spring constant. A sensor 28 is positioned between the lower frame 20 and the upper frame 22. The sensor can be in the nature of a linear variable differential transformer which is installed to connect the lower frame 20 in the upper frame 22. This linear variable differential transformer measures the dynamic displacement between the wheel 14 in contact with the underlying surface 12 and the vehicle body. In the present invention, the linear variable differential transformer is monitored constantly to measured the displacement between the lower frame 20 and the upper frame 22 of the vehicle 18.

In the system 10 of the present invention, there is a base 30 that is mounted to the vehicle 18. In FIG. 1, it can be seen that the base 30 is mounted to the lower frame 20. However, within the concept of the present invention, the base 30 can be mounted to any location on the vehicle 10 generally in a location adjacent to the wheel 14. The base 30 includes a first laser 32, a second laser 34 and a third laser 36. The first laser 32 serves to direct a laser beam 38 (illustrated in broken line fashion) toward the underlying surface 12 in an area adjacent to the wheel 14. The second laser 34 directs a laser beam 40 in transverse relationship to the base 30 and in a direction substantially vertical. The laser beam 40 is directed toward the underlying surface 12. The second laser 34 is positioned in spaced relationship to the first laser 32. The third laser 36 is affixed to the base 30 and serves to direct a laser beam 42 toward the underlying surface 12. The third laser 36 is positioned in spaced relationship to the second laser 34. The third laser 36 is located on the side of the second laser 34 opposite to that of the first laser 32.

In FIG. 1, it can be seen that the first laser 32 has a point of reflectance 44 in spaced relationship to the point of reflectance 46 of the laser beam 40. The laser beam 42 has a point of reflectance 48 at the underlying surface 12 that is spaced from the point of reflectance 46 of the laser beam 40. As will be described hereinafter, the measurement of the distances between the point of reflectance 44 and the point of reflectance 46, along with the measurement of the distance between the point of reflectance 46 and the point of reflectance 48, can provide an indication of the angular deflection of the underlying surface 12.

In FIG. 1, it can be seen that a camera 50 is mounted adjacent to the base 30. The camera 50 should be suitably positioned or directed so as to focus on the generalized area of the points of reflectance 44, 46 and 48. As such, as the vehicle 18 travels along the underlying surface 12, the camera 50 will produce images that capture the points of reflectance 44, 46 and 48. The camera 50 is connected by line 52 to a processor 54. As will be described hereinafter, processor 54 will process the images as transmitted by the camera 50 so as to evaluate the measured distances between the points of reflectance 44, 46 and 48 so as to produce an output that is indicative of the deflection and slope of the underlying surface 12.

In the present invention, so as to properly compensate for the dynamic forces generated by loads on the vehicle 18 such as loads created by crosswinds upon the vehicle 18, along with other forces, the sensor 28 is also coupled to the processor 54. The force applied to the springs 24 and 26 is measured by the formula:

$$F = kX$$

In this formula, F is the force, k is the spring constants of the springs 24 and 26, and X is the displacement of the combined springs 24 and 26. The constant k can be directly measured for each vehicle 18 by placing variable known weights on it and measuring the resulting spring displacement. When applied to these concepts, the force on the load wheel 14 is known through the equation where X is measured by the linear variable differential transformer sensor 28 and the spring constant K. By this technique, it is important to note that the spring constant k need not be linear. It just needs to be evaluated over the range of displacements experienced by normally operated vehicles 18. As such, the evaluation of the deflection 16 of the underlying surface 12 can be based upon the measured angle of deflection along with the determined loads caused by the vehicle 18 or experienced by the vehicle 18. Multiple sets of lasers and cameras may be attached to the base 30 at a known displacement from the wheel 14 to measure the variation of displacement and deflection slope to determine the shape of the deflection basin.

Figure 2:
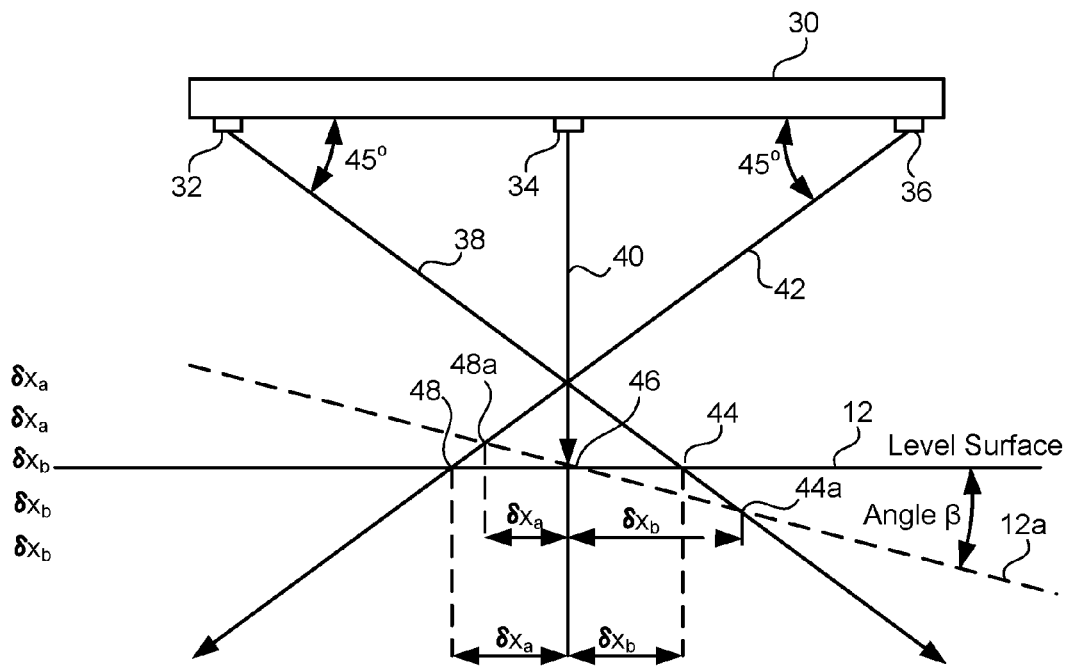
FIG. 2 is a graphical illustration showing the transmission of the laser beams toward the underlying surface.

FIG. 2 illustrates how the evaluation of the angle of deflection of the underlying surface 12 is determined. In FIG. 2, the base 30 is particularly illustrated as having the first laser 32, the second laser 34, and the third laser 36. The first laser 32 is directed at an identical angle to that of the third laser 36. In particular, the angle at which the first laser 32 is directed is 45°. Similarly, the third laser 36 is directed at a 45° angle. The second laser 34 directs its beam in transverse relationship to the base 30. In particular, the beam 38 from the first laser 32 will contact the underlying surface at point of reflectance 44. The beam 40 from the second laser 32 will contact the underlying surface at the point of reflectance 46. The beam 42 will contact the underlying surface 12 at the point of reflectance 48. In particular, as illustrated in FIG. 2, the distance between the point of reflectance 44 and the point of reflectance 46 is indicated by $\delta x_b$. the distance between the point of reflectance 46 and the point of reflectance 48 is illustrated by the distance $\delta x_a$.

When the underlying surface 12 is an underlying surface 12a, then the point of reflectance 48 of the beam 42 will be at 48a. The point of reflectance of the beam 40 will be in the same position as point of reflectance 46. The point of reflectance of the beam 38 will be at point 44a. When the underlying surface 12a is deflected in the manner shown by the broken line in FIG. 2, then the point of reflectance be 48a will be separated from the point of reflectance 46 by $\delta x_a$. The point of reflectance 46 will be spaced from the point of reflectance 44a by $\delta x_b$. These distances can be compared in order to produce the angle of deflection β.

FIG. 2 illustrates that when the target is inclined at the angle β relative to the base 12, then $\delta x_b$ is greater than $\delta x_a$. As such, the greater angle of inclination is created.

Figure 3:
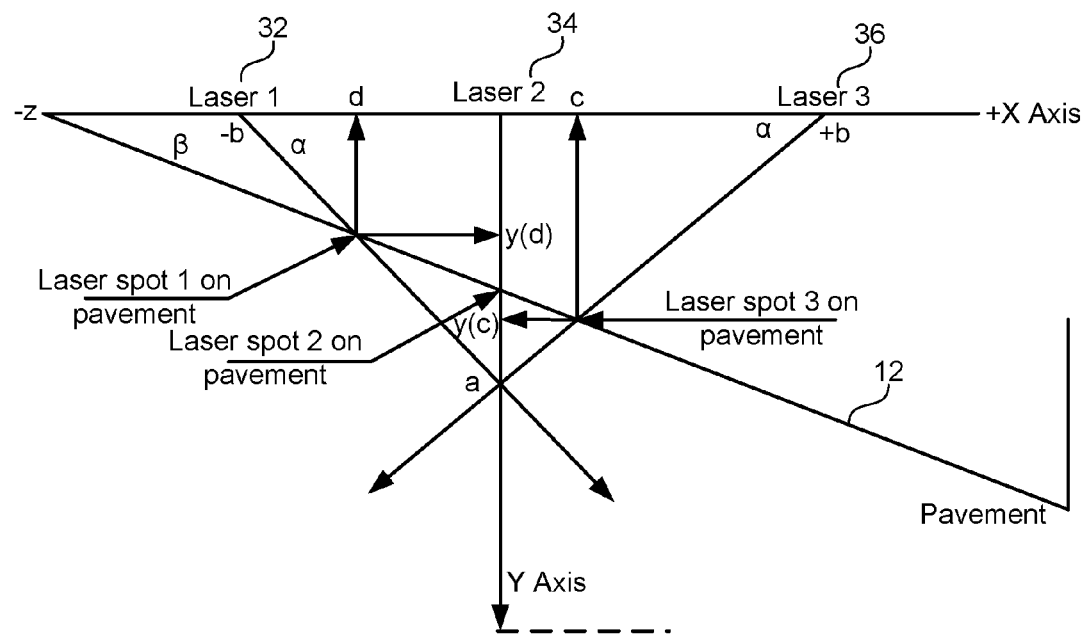
FIG. 3 is a diagrammatic illustration of the transmission of the laser beams toward the underlying surface for the purposes of calculating an angle of deflection.

FIG. 3 details the relationship between the lengths d and c between the points of reflectance. In particular, the inclination angle β can be calculated accordance with the following formula:

$$\mathrm{Tan}(\beta) = -\mathrm{Tan}(\alpha) \times (c-d)/(c+d)$$

The ratio between these distances will serve to measure the angle between the pavement and the base 30 holding the lasers 32, 34 and 36. The advantage of measuring the slope of the pavement, as opposed to measuring the distance between the lasers in the pavements is the ratio $K*(c-d)/(c+d)$ with K being the tangent of the known angle α is constant and independent of the actual elevation of the lasers above the pavement. Hence, the slope of the deflection surface can be measured accurately independently of the vertical variation of elevation (i.e. caused by vertical vibration) between the lasers mounted on a moving vertically-vibrating vehicle and the reflecting surface. By shifting the pavement quality criteria from deflection magnitude to the slope of the deflection curve, the vertical vibration noise component is eliminated. An immediate application is to a track modulus measurement by eliminated the vertical vibration noise. This should allow for data collection well over ten miles per hour.

Figure 4:
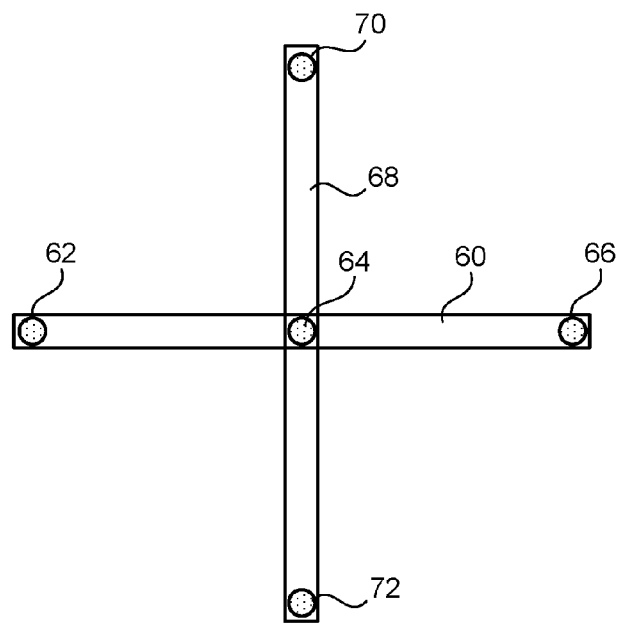
FIG. 4 is a plan view showing an alternative embodiment of the present invention.

FIG. 4 shows an alternative embodiment of the present invention employing a total of five (5) lasers. In particular, there is a first base 60 having a generally linear configuration. The first base 60 includes a first laser 62, a second laser 64, and a third laser 66. Another base 68 extends transverse relationship to the first base 60. The second base 68 includes a fourth laser 70 and a fifth laser 72. The first base 60, along with lasers 62, 64 and 66, will have a configuration similar to that described herein previously. The fourth laser 70 will be spaced from the second lasers 64. The fourth laser 70 will be directed toward the second laser 64 at an acute angle relative to the second base 68. The fifth laser 72 is located on opposite side of the second laser 64 from the fourth laser 70. Laser 72 can also be directed in an acute angle toward the second laser 64.

The configuration of five lasers, as shown in FIG. 4, provides additional information relative to the quality of the deflection caused by the load wheel 12. In particular, whenever a deflection in the pavement surface occurs, a basin is created having a length and a width. In other words, the basin deflects in both the x direction and in the y direction. Lasers 70 and 72, in combination with laser 64, can determine the extent of deflection in the y direction. As such, the addition of these further lasers measures the angle of a two dimensional target surfaces. In this configuration, the first, third, fourth and fifth lasers are aimed at the spot on the target from the second laser. The second laser will stay oriented at a right angle relative to the bases 60 and 68.

Figure 5:
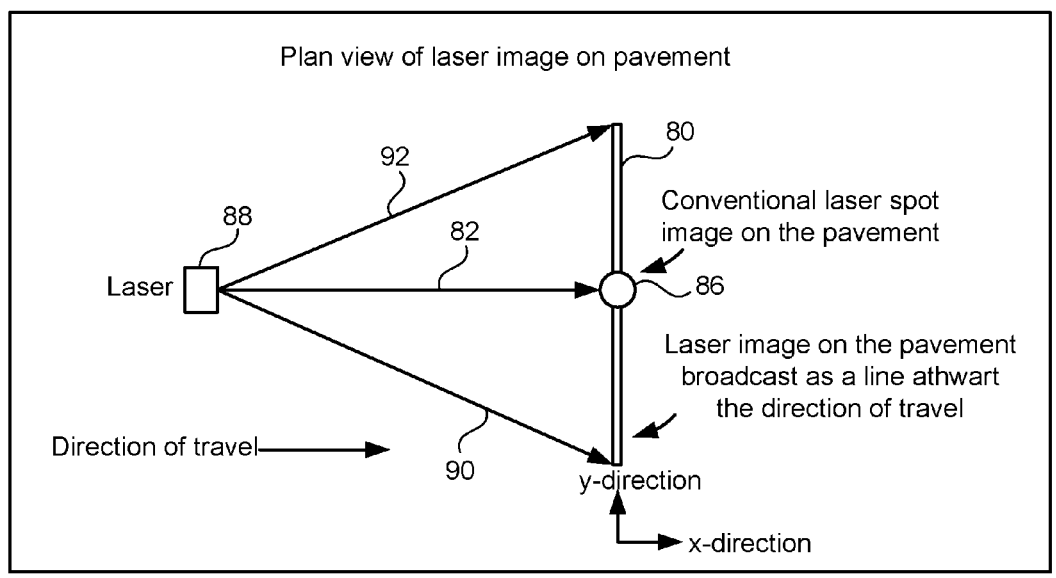
FIG. 5 is a diagram showing the application of the present invention for the purpose of addressing surface irregularities on the pavement surface.

Another major contributor to errors in measuring either distance to target or inclination of target is the texture of the target surface. In many applications, the texture of the surface is comparable to the laser spot diameter so as to create an irregular or blotchy reflection pattern that is difficult to accurately measure. In order to address this texture problem, to solve this problem the laser spot is replaced with a line source illustrated in FIG. 5. Laser beam 82 creates a spot 86 on the underlying surface 80. However, the laser 88 in the present invention can broadcast a line source along the underlying surface 80 from laser beams 90 and 92. The laser line extends from where beams 90 and 92 intersect the surface 80. The laser image on the pavement is broadcast as a line of athwart the direction of travel of the vehicle. The line image recorded by the digital camera is a matrix of pixels. Each pixel records the intensity of the reflected light incident on the individual pixel. By summing the pixels from a line to a spot, the shadow effect of texture is minimized and the position of the spot image is enhanced. Since the tops and valleys of the rough pavement surface are essentially random, with the tops predominating, then the method to overcome this noise effect is spacial averaging. This averaging is athwart the direction of travel to keep the laser beam as narrow as possible in the measurement direction. In particular, the laser sources modified from spots 86 of the prior art to a line (illustrated by the line from 90 to 92) that is broadcast athwart the direction of the vehicle travel. This makes feasible the summing of the image intensities in the Y direction over an adequate number of conventional laser beam diameters so as to achieve a high signal-to-noise ratio and accurate measurement.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A system for measuring a deflection of an underlying surface, the system comprising:
a base;
a first laser affixed to said base, said first laser directed downwardly toward the underlying surface at an acute angle relative to said base;
a second laser affixed to said base and positioned in spaced relationship and on one side of said first laser, said first laser directed downwardly in a direction toward said second laser, said second laser directed downwardly toward the underlying surface at an angle approximately transverse to said base;
a third laser affixed to said base and positioned in spaced relation to said second laser on a side of said second laser opposite said first laser, said third laser directed downwardly toward underlying surface at the same acute angle relative to said base and in a direction toward said second laser;
a camera directed downwardly toward the points of reflectance of said first laser and said second laser and said third laser with the underlying surface; and
a processor cooperative with said camera so as to measure a distance between the point of reflectance of said first laser with the underlying surface and the point of reflectance of said second laser with respect to said underlying surface and so as to measure a distance between the point of reflectance of said second laser with the underlying surface and the point of reflectance of said third laser, said processor comparing the measured distances so as to produce an angle of deflection of the underlying surface.

2. The system of claim 1, further comprising:
a vehicle having at least one wheel, said vehicle having a frame, said base affixed to said frame such that said first laser and said second laser and said third laser are directed toward the underlying surface adjacent the wheel.

3. The system of claim 2, said vehicle being in a truck, the underlying surface being a pavement.

4. The system of claim 2, said vehicle being a train, the underlying surface being a rail.

5. The system of claim 1, the acute angle of said first laser being identical to the acute angle of said third laser.

6. The system of claim 1, the acute angle of said first laser being approximately 45°, the acute angle of said third laser being approximately 45°.

7. The system of claim 2, said camera obtaining a plurality of images of the points of reflectance of said first laser and said second laser and said third laser as said vehicle moves along the underlying surface.

8. The system of claim 7, said processor comparing the measured distance of a first image and a second image of said plurality of images so as to produce the angle of deflection.

9. The system of claim 5, said processor determining the angle of deflection in accordance with a formula:

$$\mathrm{Tan}(\beta) = -\mathrm{Tan}(\alpha) \times (c-d)/(c+d)$$

where $\beta$ is the angle of deflection, $\alpha$ is the acute angle of said first and second lasers, c is the distance between the points of reflectance of said first laser and said second laser and d is the distance between the points of reflectance of said second laser and said third laser.

10. The system of claim 1, further comprising:
a crossmember extending in transverse relation to said base;
a fourth laser affixed to said crossmember directed downwardly toward the underlying surface in a direction toward said second laser, said fourth laser being in spaced relationship to said second laser; and
a fifth laser affixed to said crossmember and directed downwardly toward the underlying surface in a direction toward said second laser, said fifth laser being in spaced relation to said second laser on a side of said second laser opposite said fourth laser.

11. The system of claim 10, said camera directed downwardly so as to capture a point of reflectance of said fourth laser with the underlying surface and to capture a point of reflectance of said fifth laser with the underlying surface.

12. The system of claim 11, said processor cooperative with said camera so as to measure a distance between the point of reflectance of said fourth laser with the underlying surface and the point of reflectance of said second laser with the underlying surface and to measure a distance between the point of reflectance of said second laser with the underlying surface and the point of reflectance of said fifth laser with the underlying surface, said processor comparing the measured distances so as to produce an angle of deflection of the underlying surface.

13. The system of claim 2, said vehicle having an upper frame and a lower frame with a spring resiliently mounted therebetween, the system further comprising:
a sensor cooperative with said upper frame and said lower frame so as to measure a displacement between said upper frame and said lower frame.

14. The system of claim 13, said processor cooperative with said sensor so as to measure a load of the wheel upon the underlying surface.

15. The system of claim 14, said processor measuring the load of the wheel in accordance $$F=kX$$

in which F is the force on the wheel, k is a spring constant of said spring, and X is the measured displacement between said upper frame and said lower frame.

16. A process for measuring a deflection of an underlying surface under a load, the process comprising:
directing a first laser toward the underlying surface at an acute angle so as to produce a point of reflectance of the first laser on the underlying surface;
directing a second laser vertically downwardly toward the underlying surface so as to produce a point of reflectance of said second laser on the underlying surface;
directing a third laser toward the underlying surface at the same acute angle and toward said second laser so as to produce a point of reflectance of said third laser on the underlying surface;
measuring a distance between the point of reflectance of said first laser and the point of reflectance of said second laser;
measuring a distance between the point of reflectance of said second laser and the point of reflectance of said third laser; and
comparing the distances so as to produce an angle of deflection of the underlying surface.

17. The process of claim 16, further comprising:
moving a vehicle along the underlying surface such that said vehicle has a wheel deflecting the underlying surface, said first laser and said second laser and said third laser connected to the vehicle, the steps of directing comprising directing said first laser and said second laser and said third laser in an area adjacent the wheel.

18. The process of claim 16, the acute angles of said first laser and said third laser being approximately equal.

19. The process of claim 17, further comprising:
measuring a load of the wheel upon the underlying surface.

20. The process of claim 19, said vehicle having an upper frame in a lower frame with a spring resiliently mounted therebetween, the step of measuring comprising:
measuring a displacement of said upper frame with said lower frame; and
comparing the measured distance with a spring constant of said spring so as to determine the load of the wheel on the underlying surface.

* * * * *